United States Patent
Romsdahl et al.

(10) Patent No.: US 6,909,797 B2
(45) Date of Patent: Jun. 21, 2005

(54) DENSITY NODULE DETECTION IN 3-D DIGITAL IMAGES

(75) Inventors: Harlan M. Romsdahl, Half Moon Bay, CA (US); Wei Zhang, Union City, CA (US); Alexander C. Schneider, Sunnyvale, CA (US)

(73) Assignee: R2 Technology, Inc., Los Altos, CA (US)

(*) Notice: Subject to any disclaimer, the term of this patent is extended or adjusted under 35 U.S.C. 154(b) by 0 days.

(21) Appl. No.: 09/993,792

(22) Filed: Nov. 23, 2001

(65) Prior Publication Data

US 2002/0141627 A1 Oct. 3, 2002

Related U.S. Application Data (63) Continuation-in-part of application No. 09/946,209, filed on Sep. 5, 2001, which is a continuation-in-part of application No. 09/907,585, filed on Jul. 17, 2001, which is a continuation of application No. 09/103,290, filed on Jun. 23, 1998, now Pat. No. 6,263,092, which is a continuation of application No. 08/676,660, filed on Jul. 10, 1996, now Pat. No. 5,815,591.

(51) Int. Cl.$^7$ ................................................ G06K 9/00
(52) U.S. Cl. ...................... 382/131; 382/172; 382/199; 356/39; 378/21
(58) Field of Search ................................ 382/128, 129, 382/130, 131, 132, 133, 197, 199, 256, 134, 169, 194, 274, 196, 270, 203, 172; 324/300, 307, 306, 313, 312, 320; 364/413.13; 378/46, 21, 98.5, 98.6; 356/39; 377/10; 250/370.09; 345/501

(56) References Cited

U.S. PATENT DOCUMENTS

| | | | | |
|---|---|---|---|---|
| 5,231,580 A | * | 7/1993 | Cheung et al. | 364/413 |
| 5,656,818 A | * | 8/1997 | Nyg.ang.rd | 250/370.09 |
| 5,815,591 A | * | 9/1998 | Roehrig et al. | 382/130 |
| 5,832,103 A | * | 11/1998 | Giger et al. | 382/130 |
| 5,889,881 A | * | 3/1999 | MacAulay et al. | |
| 5,937,083 A | * | 8/1999 | Ostuni | |
| 6,198,838 B1 | * | 3/2001 | Roehrig et al. | 382/132 |
| 6,327,377 B1 | * | 12/2001 | Rutenberg et al. | 382/133 |

* cited by examiner

*Primary Examiner*—Bhavesh M. Mehta
*Assistant Examiner*—Seyed Azarian
(74) *Attorney, Agent, or Firm*—Morgan, Lewis & Bockius LLP

(57) ABSTRACT

An algorithm is quickly scans a digital image volume to detect density nodules. A first stage is based on a transform to quickly highlight regions requiring further processing. The first stage operates with somewhat lower sensitivity than is possible with more detailed analyses, but operates to highlight regions for further analysis and processing. The transform dynamically adapts to various nodule sizes through the use of radial zones. A second stage uses a detailed gradient distribution analysis that only operates on voxels that pass a threshold of the first stage.

27 Claims, 8 Drawing Sheets

DENSITY NODULE DETECTION IN 3-D DIGITAL IMAGES

This application is a continuation-in-part of co-pending application Ser. No. 09/946,209 filed Sep. 5, 2001 which is a CIP of application Ser. No. 09/907,585 filed Jul. 17, 2001 which in turn is a continuation of Ser. No. 09/103,290 filed on Jun. 23, 1998, now U.S. Pat. No. 6,263,092, which in turn is a continuation of Ser. No. 08/676,660, filed on Jul. 10, 1996, now U.S. Pat. No. 5,815,591.

CROSS-REFERENCE TO RELATED APPLICATIONS

Related applications are:

"Method and System for the Display of Regions of Interest in Medical Images," Ser. No. 09/990,508, filed Nov. 21, 2001;

"Vessel Segmentation with Nodule Detection," filed concurrently herewith;

"Automated Registration of 3-D Medical Scans of Similar Anatomical Structures," filed concurrently herewith;

"Lung Field Segmentation From CT Thoracic Images," filed concurrently herewith;

"Pleural Nodule Detection from CT Thoracic Images," filed concurrently herewith; and "Graphical User Interface for Display of Anatomical Information," Ser. No. 09/990,511, filed Nov. 21, 2001, claiming priority from Serial No. 60/252,743, filed Nov. 22, 2000 and from Serial No. 60/314,582 filed Aug. 24, 2001.

This application hereby incorporates by reference the entire disclosure, drawings and claims of each of the above-referenced applications as though fully set forth herein.

FIELD OF THE INVENTION

The present invention relates to the field of computer-aided detection of abnormal lesions and features in digital images. In particular, the invention relates to a fast algorithm for detecting possible anatomical abnormalities that may be overlooked in digital medical images.

BACKGROUND OF THE INVENTION

The diagnostically superior information available from data acquired from various imaging systems, especially that provided by multidetector CT (multiple slices acquired per single rotation of the gantry) where acquisition speed and volumetric resolution provide exquisite diagnostic value, enables the detection of potential disease problems at earlier and more treatable stages. Given the vast quantity of detailed data acquirable from imaging systems, various algorithms must be developed to efficiently and accurately process image data. With the aid of computers, advances in image processing are generally performed on digital or digitized images.

Digital acquisition systems for creating digital images include digital X-ray film radiography, computed tomography ("CT") imaging, magnetic resonance imaging ("MRI") and nuclear medicine imaging techniques, such as positron emission tomography ("PET") and single photon emission computed tomography ("SPECT"). Digital images can also be created from analog images by, for example, scanning analog images, such as typical x-rays, into a digitized form. Further information concerning digital acquisition systems is found in our above-referenced copending application "Graphical User Interface for Display of Anatomical Information".

Digital images are created from an array of numerical values representing a property (such as a grey scale value or magnetic field strength) associable with an anatomical location referenced by a particular array location. In 2-D digital images, or slice sections, the discrete array locations are termed pixels. Three-dimensional digital images can be constructed from stacked slice sections through various construction techniques known in the art. The 3-D images are made up of discrete volume elements, also referred to as voxels, composed of pixels from the 2-D images. The pixel or voxel properties can be processed to ascertain various properties about the anatomy of a patient associated with such pixels or voxels.

Once in a digital or digitized format, various analytical approaches can be applied to process digital anatomical images and to detect, identify, display and highlight regions of interest (ROI). For example, digitized images can be processed through various techniques, such as segmentation. Segmentation generally involves separating irrelevant objects (for example, the background from the foreground) or extracting anatomical surfaces, structures, or regions of interest from images for the purposes of anatomical identification, diagnosis, evaluation, and volumetric measurements. Segmentation often involves classifying and processing, on a per-pixel basis, pixels of image data on the basis of one or more characteristics associable with a pixel value. For example, a pixel or voxel may be examined to determine whether it is a local maximum or minimum based on the intensities of adjacent pixels or voxels.

Once anatomical regions and structures are constructed and evaluated by analyzing pixels and/or voxels, subsequent processing and analysis exploiting regional characteristics and features can be applied to relevant areas, thus improving both accuracy and efficiency of the imaging system. For example, the segmentation of an image into distinct anatomical regions and structures provides perspectives on the spatial relationships between such regions. Segmentation also serves as an essential first stage of other tasks such as visualization and registration for temporal and cross-patient comparisons.

Key issues in digital image processing are speed and accuracy. For example, the size of a detectable tumor or nodule, such as a lung nodule, can be smaller than 2 mm in diameter. Moreover, depending on the particular case, a typical volume data set can include several hundred axial sections, making the total amount of data 200 Megabytes or more. Thus, due to the sheer size of such data sets and the desire to identify small artifacts, computational efficiency and accuracy is of high priority to satisfy the throughput requirements of any digital processing method or system.

Accordingly, it is an object of the present invention to provide a fast, yet accurate, computer-assisted diagnosis ("CAD") system for assisting in the identification of suspicious masses and tissue in digital images, the CAD system being capable of producing an output which directs attention to suspicious portions of digital images. It is an object of the invention to provide such systems and methods for processing digital images that can effectively and quickly identify regions of the image containing suspicious features requiring further consideration and evaluation. It is a further object of the invention to provide a system and method for detecting nodules. It is a further object of the invention to provide a nodule detection approach that can be adapted to perform on or compensate for partial volumes or data sets. It is a further object to provide a nodule detection process and system that is adaptable for a large range of anatomical regions for processing yet is fast enough to permit use of the CAD system in a clinical radiology environment.

The foregoing and other problems are overcome by methods and apparatus in accordance with embodiments of this invention.

SUMMARY OF THE INVENTION

These and other objects of the present invention are provided for by an improved CAD system and method for rapidly detecting nodules and other suspicious features from digital images. A CAD system according the present invention employs a fast method for detecting suspicious regions from digital images, the method including steps for determining an array of potential intersections from a plurality of voxels using vector information. The vector information is obtained from a plurality of voxels to produce a cumulative multidimensional array. Using information derived from the cumulative array, such as the directions, positions and strengths of local maxima for identifying nodules and other suspicious matter, anatomical information associated with a digital image or volume can be derived. The approach effectively has several distinct stages.

A first stage uses digital image processing techniques to quickly highlight regions requiring further and more detailed processing. The first stage operates with somewhat lower sensitivity than is possible with other more detailed analyses. In this way, computation resources can be more effectively applied to areas of concern.

A second stage uses a detailed gradient distribution analysis that only operates on voxels identified by the first stage. Effectively, the second stage provides higher resolution analysis of the regions identified by the first stage.

Since the first stage effectively and quickly identifies regions for further processing, the combination of the first stage analysis with the additional processing of second stage results in a fast yet effective overall algorithm to identify potential anatomical abnormalities from digital volumes.

BRIEF DESCRIPTION OF THE FIGURES

These and other objects and advantages of the present invention will be more readily apparent from the following detailed description of a preferred embodiment of the invention in which.

DETAILED DESCRIPTION OF THE INVENTION

The present invention provides for systems and methods capable of effective and accurate detection of suspicious features identified from 2-D and 3-D digital images. A 3-D digital volume can be generated from the 2-D slices by any one of various techniques known in the art. The terms "digital" and "digitized" as used herein will refer to images or volumes, as appropriate, in a digital or digitized format acquired via a digital acquisition system or via conversion from an analog image.

The digital image sections and volumes to be processed, rendered, displayed or otherwise used include digitized images acquired through any plane, including, without limitation, saggital, coronal and axial (or horizontal, transverse) planes and including planes at various angles to the saggital, coronal or axial planes. While the disclosure may refer to a particular plane or section, such as an axial section or plane, it is to be understood that any reference to a particular plane is not necessarily intended to be limited to that particular plane, as the invention can apply to any plane or planar orientation acquired by any digital acquisition system.

Figure 1:
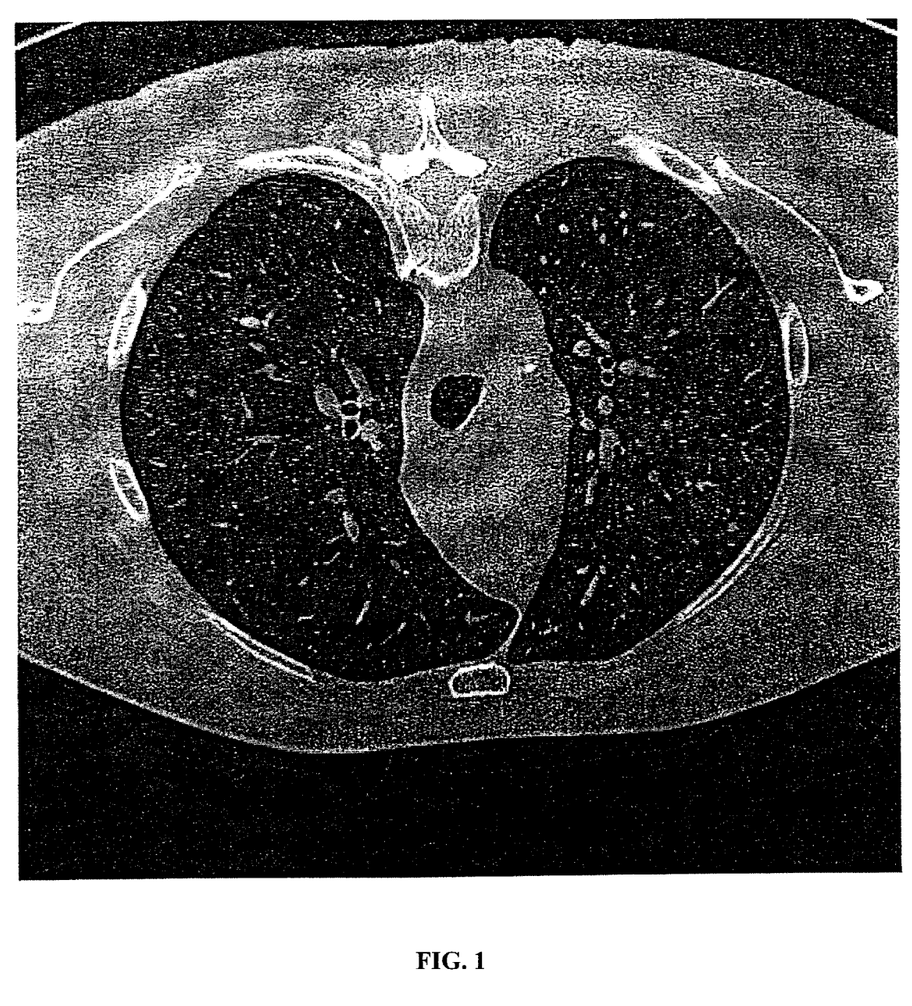
FIG. 1 depicts an axial section of a CT digital image section.

The present invention is preferably performed on a computer system, such as a Pentium™-class personal computer, running computer software that implements the algorithm of the present invention. The computer includes a processor, a memory and various input/output means. A series of CT axial or other digital images representative of an anatomical volume are input to the computer for processing by a detection algorithm. Examples of a digital image or section is shown in FIG. 1.

The purpose of the detection algorithm is to quickly scan an input image volume generated from the digital images, highlight initial ROIs and process the ROI to detect, identify or otherwise provide detailed information regarding lesions, nodules or other suspicious anatomical features. Identified ROIs can be used, for example, to highlight regions for purposes of display, temporal comparison or for further processing. ROIs can also be used to segment the nodule in the original volume for further analysis.

Various techniques are available for processing digital images to identify features and ultimately to identify ROIs. For example, various intermediate-level processes can be performed for line detection, circle detection, hole detection and corner detection (for various discussion and details regarding intermediate-level processing see, for example, E. R. Davies, *Machine Vision: Theory, Algorithms, Practicalities*, 2$^{nd}$ Ed., Academic Press, 1997, pgs. 195–343, incorporated herein by reference).

One such technique which is described in greater detail in copending application Ser. No. 09/907,585 and columns 9 through 12 of U.S. Pat. No. 6,263,092 is useful in processing structural information in digital images. In the '092 patent, this technique is used to detect speculated, or stellar-shaped, lesions in mammograms. Since a spiculation is a roughly symmetric set of lines radiating from a central point or region, the spiculations can be located by locating the lines and projecting the lines to their point of intersection. Such points of intersection are identified by use of a cumulative array.

Figure 2:
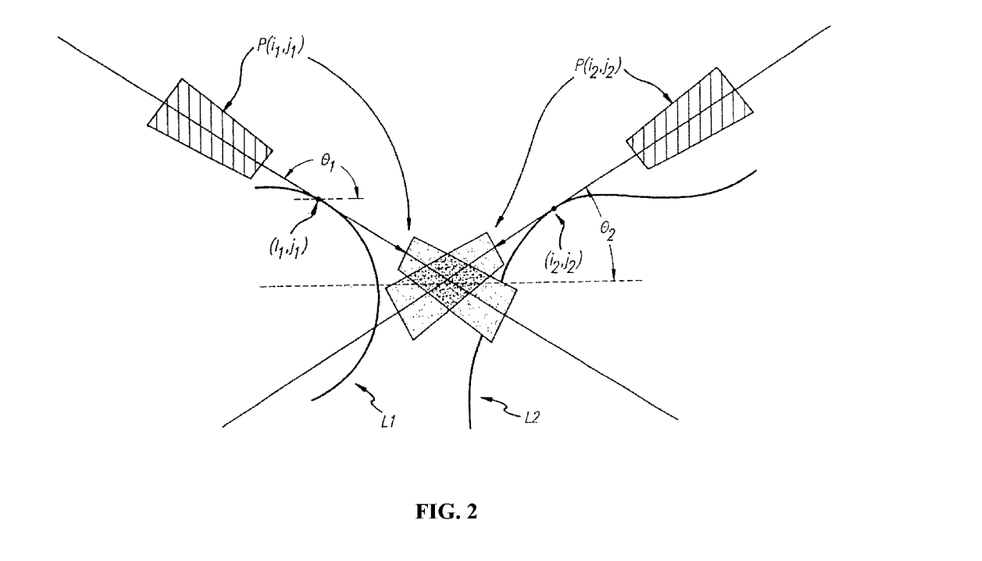
FIG. 2 is a conceptual diagram showing the determination of potential regions of intersection for two points in a line image in accordance with the present invention, the two lines not being associated with a common nodule.
Figure 3:
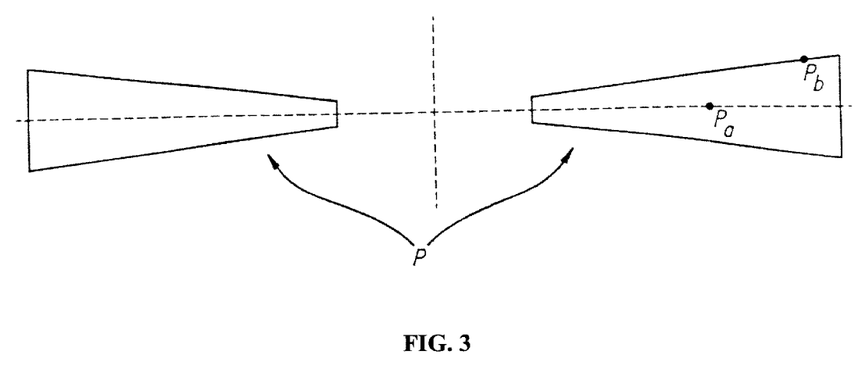
FIG. 3 shows a typical predetermined pattern P used to generate regions of potential intersection in the nodule detection algorithm according to the present invention.
Figure 4:
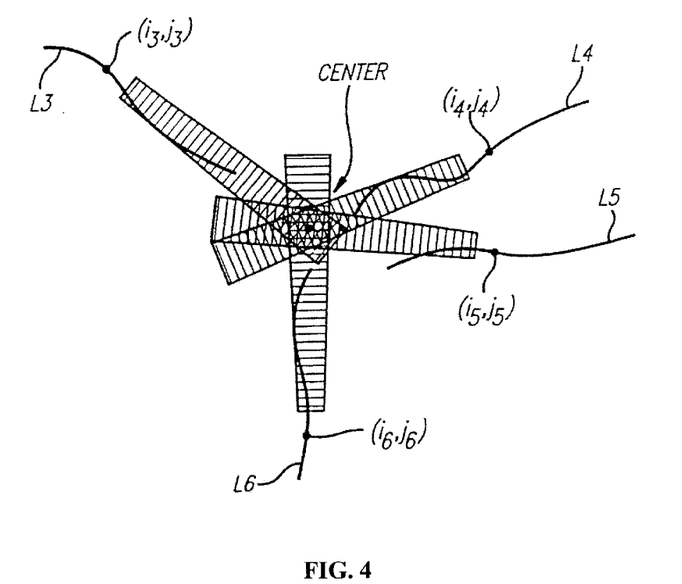
FIG. 4 is a conceptual diagram showing the determination of potential regions of intersection for two points in a line image in accordance with the present invention, the two lines being associated with a common nodule.

This process is illustrated in FIGS. 2, 3 and 4 which are reproduced from FIGS. 7, 8 and 9 of the '092 patent. The process begins by initializing a cumulative array C. The array has the same size and coordinate system as the digital image and the digital image, shown in FIG. 2 can be thought of as superimposed on the cumulative array. Following initialization, each pixel (i, j) in the digital image is considered in turn. If there is no line information in the pixel, the pixel is ignored. If, however, there is line information in the pixel, the cumulative array is incremented at certain locations defined by a predetermined pattern P centered at the projection of the pixel location (i, j) onto the cumulative array. After each pixel in the digital image is considered, the cumulative array C is completely formed. The array is then examined to locate those points having the highest values and these points are associated with the centers of spiculations.

FIG. 2 is a conceptual diagram illustrating such processing of a 2-D digital image. Shown in FIG. 2 are two points (i1,j1) and (i2,j2) that lie somewhere along lines L1 and L2, respectively. The detection algorithm as applied to pixel-by-pixel analysis is based on the principle that any two lines L1 and L2 belonging to the same nodule or spiculation will have an entire series of points (i1,j1) and (i2,j2) whose tangents will overlap near a common point at the center of the spiculation or nodule. Regions of potential overlap for these two points, denoted P(i1,j1) and P(i2,j2), are shown superimposed over the line image for clarity. The regions of potential overlap P(i1,j1) and P(i2,j2) are simply rotated versions of a predetermined pattern P, shown in FIG. 3, which have been translated to be centered on the points (i1,j1) and (i2,j2), respectively. As shown in FIGS. 2 and 3, the predetermined pattern P is of a split rectangular or trapezoidal shape having a high aspect ratio (i.e., a large width to height ratio). For each point on a line, the cumulative array is incremented within the region of potential overlap as projected onto the cumulative array.

As can be seen in FIG. 2, the region of potential overlap P(i1,j1) for the point (i1,j1) is roughly equivalent to a tangent of the line L1 containing the point (i1,j1), the tangent having been truncated at a distance corresponding to the length of the pattern P. Similarly, the region of potential overlays P (i2,j2) for the point (i2,j2) is roughly equivalent to a tangent of the L2 containing the point (i2,j2). In FIG. 2, the lines denoted L1 and L2 do not belong to a nodule or spiculation, and it can be seen that the regions of pattern overlap for various points (i1,j1) and (i2,j2) along lines L1 and L2 will be projected onto many locations in the cumulative array C. Thus, the cumulative array will be incremented relatively uniformly.

In contrast, as shown in FIG. 4, lines L3, L4, L5, and L6, having pixels including exemplary pixels (i3,j3), (i4,j4), (i5,j5), and (i6,j6), respectively, belonging to the same spiculation or nodule will have repeated overlap of tangents near the center of the spiculation or nodule.

Accordingly, if the regions of potential overlap, denoted generally as P(x,y), are accumulated into the cumulative array C, the cumulative array C will contain higher values at locations corresponding to regions of possible abnormality. The greater the number of intersecting, radiating lines at an abnormality, the greater the value of the cumulative array C.

Importantly, this pixel-based detection algorithm is a "forward direction" algorithm in that each pixel in the line image is processed only once in generating the cumulative array C. Furthermore, a lookup table procedure may be used which directly maps the digital mammogram pixels (i,j) lying along lines and having direction values into regions of covered pixels in the cumulative array C, based on the shape of the predetermined pattern P.

The lookup table procedure for mapping points and directions into regions of potential intersection may also incorporate weighting values in the predetermined pattern P. Thus, instead of simply adding a "1" to the cumulative array C for every array location falling inside the pattern P(i1,j1), a weighting value may be used. For example, points corresponding to a point $P_a$ in the predetermined pattern P of FIG. 4, lying directly along the center line of P, may be assigned a heavier weight than a point $P_b$ lying along the periphery of the predetermined pattern P. This is because peripheral points are less likely than center line points to lie directly at the center of the abnormality.

The predetermined pattern P is designed in an empirical manner to maintain accuracy (minimizing false positives) while maximizing precision in finding abnormalities of the appropriate size. In one example, it may be desirable to detect abnormalities which have a radius of around 5 mm, because if the abnormalities grow to a size much larger than a 5 mm radius, it may be too late to stop the spread of the cancer. For a digital image in which 1 pixel corresponds to 200 microns, or in which 25 pixels equals 5 mm, it has been found that a predetermined pattern P having its opposing trapezoids extending from about 15 pixels to about 80 pixels from the center, with a width ranging from about 4 pixels near the center to 20 pixels at the periphery, yields satisfactory results.

While the above discussion regarding FIGS. 2–4 has described detection of radiating lines in 2-D images, a similar analysis can be applied to detection of gradients in 3-D images. A similar procedure to the pixel-based process wherein an operation is performed on a pixel and the resulting information is effectively disbursed to adjacent pixels can be made to apply to voxels.

Regions of potential overlap in 3-D may be translated to be centered on the points (x1, y1, z1) and (x2, y2, z2), respectively, the amount of rotation being a gradient or direction image value for voxel (x1, y1, z1) and for voxel (x2, y2, z2).

The detection algorithm as applied to voxel-by-voxel analysis is based on the principle that any intensity regions belonging to the same nodule will have an entire series of points in 3-D whose gradient component will overlap near a common point at the center of the spiculation or nodule.

Accordingly, if the regions of potential overlap, denoted generally as P(x, y, z), are accumulated into a cumulative array C', the cumulative array C' will contain higher values at locations corresponding to regions of possible abnormality. The greater the number of overlapping regions, or bins, at an abnormality, the greater the value of the cumulative array C'.

In one embodiment of the present invention, an edge of the nodule is represented by vector that estimates characteristics of the nodule such as size, contrast, sharpness and shape. Vector information obtained from various voxels can be aggregated to provide further details and characteristics of a nodule.

Figure 5:
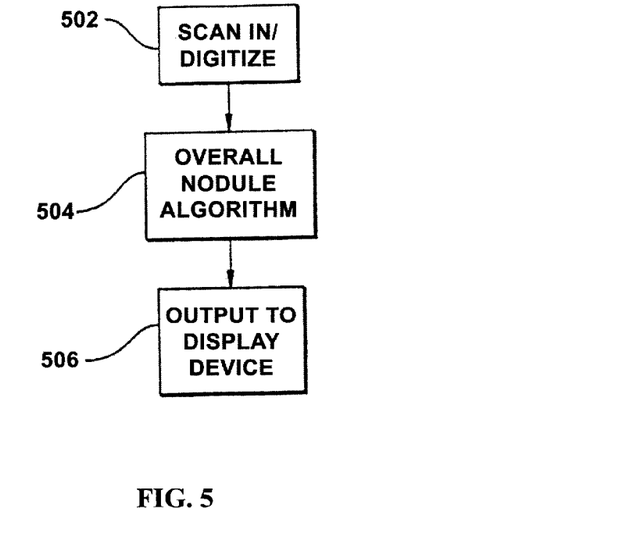
FIG. 5 is a flowchart representing overall steps practiced by the system of the present invention.

FIG. 5 shows the general steps performed by a CAD processing unit on digital images in accordance with the invention. At step 502, images are either digitized or received in a digital format from a digital acquisition system. The digital images may be, for example, a 3000×4000 array of 12-bit gray scale pixel values.

FIG. 5 shows the digital image being processed at step 504 by an overall nodule detection algorithm in accordance with the present invention. The overall nodule detection algorithm performed at step 504 includes a stage for generating or otherwise highlighting locations in the digital image or digital volume which may correspond to nodules, along with information, such as nodule intensity, for each location. Following step 504, the digital image and list of nodule locations and information is output for display at step 506.

Figure 6:
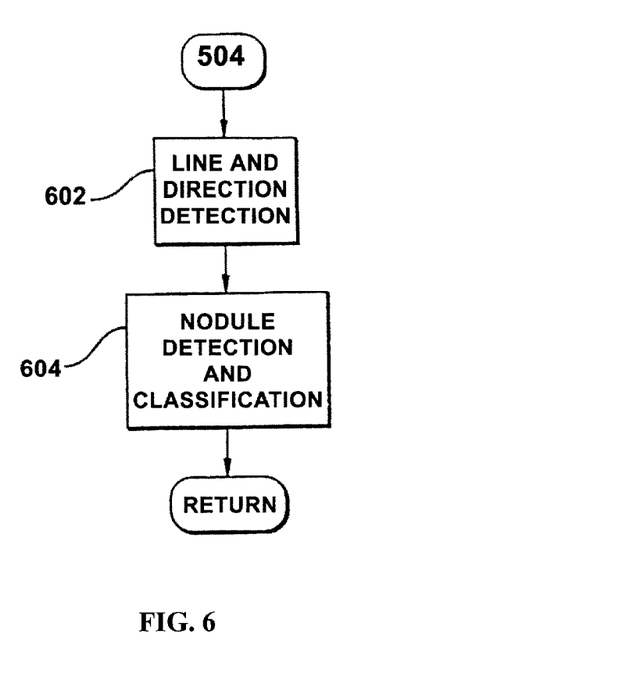
FIG. 6 is a process flow chart of one embodiment of the present invention.

FIG. 6 shows in more detail the steps associated with the overall nodule detection algorithm of step 504 of FIG. 5. The nodule detection algorithm herein is based on generating local intensity gradient vectors from digital pixels for 2-D curves and from digital voxels for 3-D curves. A gradient vector is the rate of change of a function per unit distance in the direction of the vector and direction of the vector is the direction of maximum rate of change of the function at that location. Changes in tissue density in a region, which may be indicative of disease in the tissue of that region, affect intensity gradients associated with the voxels of a region's digital image.

Gradient vectors taken at the edge of a nodule contain nodule orientation information. A plurality of edge gradient vectors can be processed to determine exact centers of the nodules. Intensity gradients and vector components of the intensity gradients are determined at step 602.

Deriving object features from gradients taken at boundaries of the objects can be performed by various transformation schemes for object detection. Different types of transformations are effective for detecting different features of an object.

As applied to information derived from image slices, an array of gradient information is generated at step 602, for each pixel (i,j) of an image slice. Pixel information is derived from vector gradients in a two-dimension space wherein directional information associated with the gradient taken at each pixel is projected onto pixels in a direction corresponding to the gradient. The process is similar to that described in connection with FIGS. 2–4. First, a cumulative array is initialized. Each pixel is considered in turn. If there is no gradient information associated with the pixel, the pixel is ignored. If, however, there is gradient information associated with the pixel, the cumulative array is incremented at certain locations defined by a predetermined pattern P that is centered at the projection of the pixel location onto the cumulative array and oriented in the direction of the gradient.

A similar process can occur for a voxel (x, y, z). Information derived from vector gradients taken in 3-D results in components in x-, y- and z-directions. Deriving gradients on a voxel-by-voxel basis at step 602 generates a multi-dimensional array containing directional information. Spherical information can be derived from vector gradients wherein directional information associated with edge gradients focus on a true center of a candidate nodule.

When scanning a volume, it is not known where a possible nodule may be located. At step 604, information of an intensity gradient calculation for a voxel is dispersed to nearby voxels through a classification procedure detailed below. The dispersed decomposition information is aggregated with information obtained from vector gradients associated with other voxels. The distribution of gradient information can then be processed to derive information relating to a volume corresponding the voxels.

Figure 7:
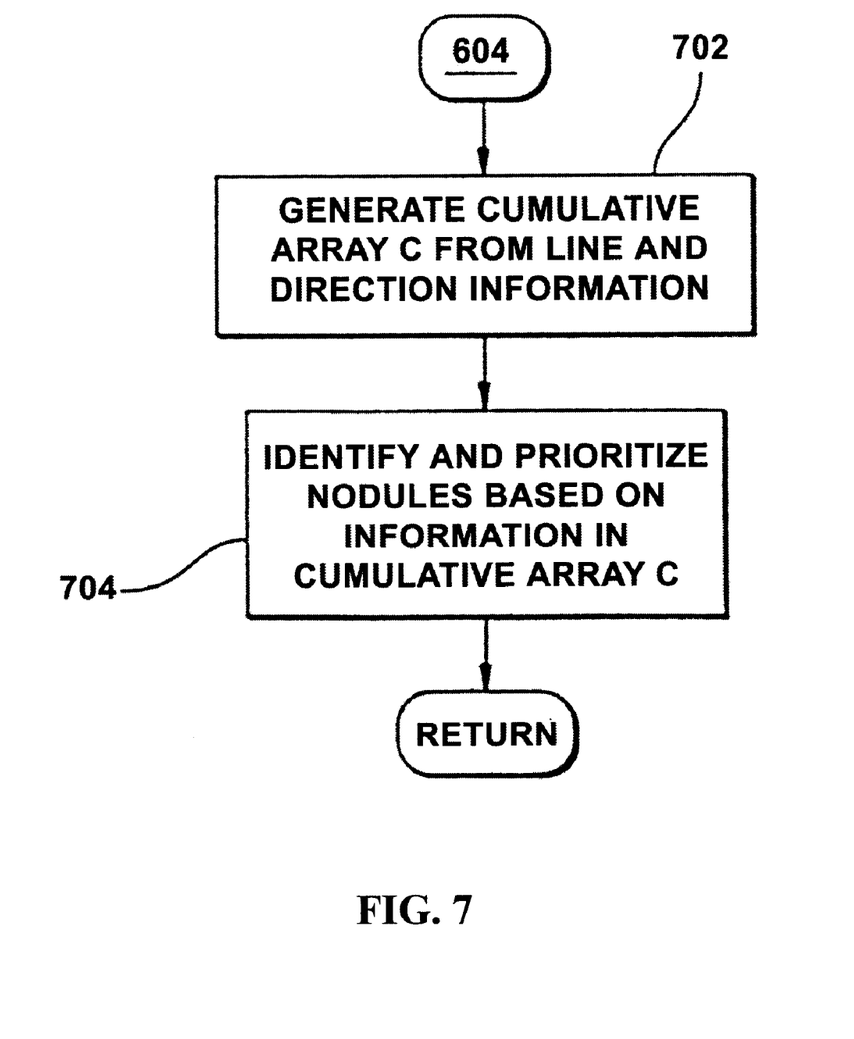
FIG. 7 is a flowchart representing a detection algorithm for the pixel-based information.

FIG. 7 shows a block diagram outlining steps for accomplishing the detection and prioritization, or classification, step 604. The process is similar to that described in conjunction with FIGS. 2–4. In 2-D, step 702 generates a cumulative array C from direction information corresponding to each pixel in the line image. The array has the same size and coordinate system as the digital image and the digital image can be thought of as superimposed on the cumulative array. The cumulative array C is first initialized. Then each pixel (i,j) in the digital image is considered. In particular, if a pixel (i,j) has no gradient information, it is ignored. However, if the pixel (i,j) has gradient information, the cumulative array C is incremented by a constant value at certain locations defined by a predetermined pattern centered at the projection of the pixel location (i,j) onto the cumulative array. After each pixel in the digital image is considered, the cumulative array C will be completely formed.

The step 702 for generating a cumulative array C from direction information corresponding to each pixel in the line image can be extended to each voxel of a digital image volume. In such a case, the cumulative array C' will have another dimension in its array to address the additional directional information and dispersion of gradient information in 3-D. Again, the cumulative array has the same size and coordinate system as the digital image so that each voxel in the digital image has a corresponding location in the cumulative array. The cumulative array is first initialized to remove, or otherwise compensate for, background noise levels. If a voxel (x, y, z) component has no intensity or density information to be dispersed or classified, it is ignored. However, if the voxel (x, y, z) has image information with a non-zero value, the cumulative array C' aggregates such information for a particular volume. Specifically, array C' is incremented by a constant value at certain locations defined by a predetermined pattern centered at the projection of the voxel location (x, y, z) into the cumulative array. After each voxel in the digital volume is considered, the cumulative array C' will be completely formed. To illustrate, the values aggregated in an array location of C' are based on intensity or density information derived from gradients for the predetermined pattern of a sphere centered at (x, y, z).

FIG. 7 further shows a step 704 for prioritizing (or classifying) information contained in the cumulative array. In 2-D, the cumulative array C will contain values C(i,j) corresponding to the strength of possible abnormalities centered on the digital mammogram pixel located at coordinates (i,j). In 3-D, the cumulative array C' will contain values C' (x,y,z) corresponding to the strength of possible abnormalities centered on the digital voxel located at coordinates (x, y, z).

The cumulative arrays C or C' can contain local maxima associated with changes in tissue density and representative of potential abnormalities. The cumulative array C or C', may be processed to identify locations and strengths of possible abnormalities in a digital image or volume. Patterns in a cumulative array can be processed to identify potential ROIs.

Figure 8:
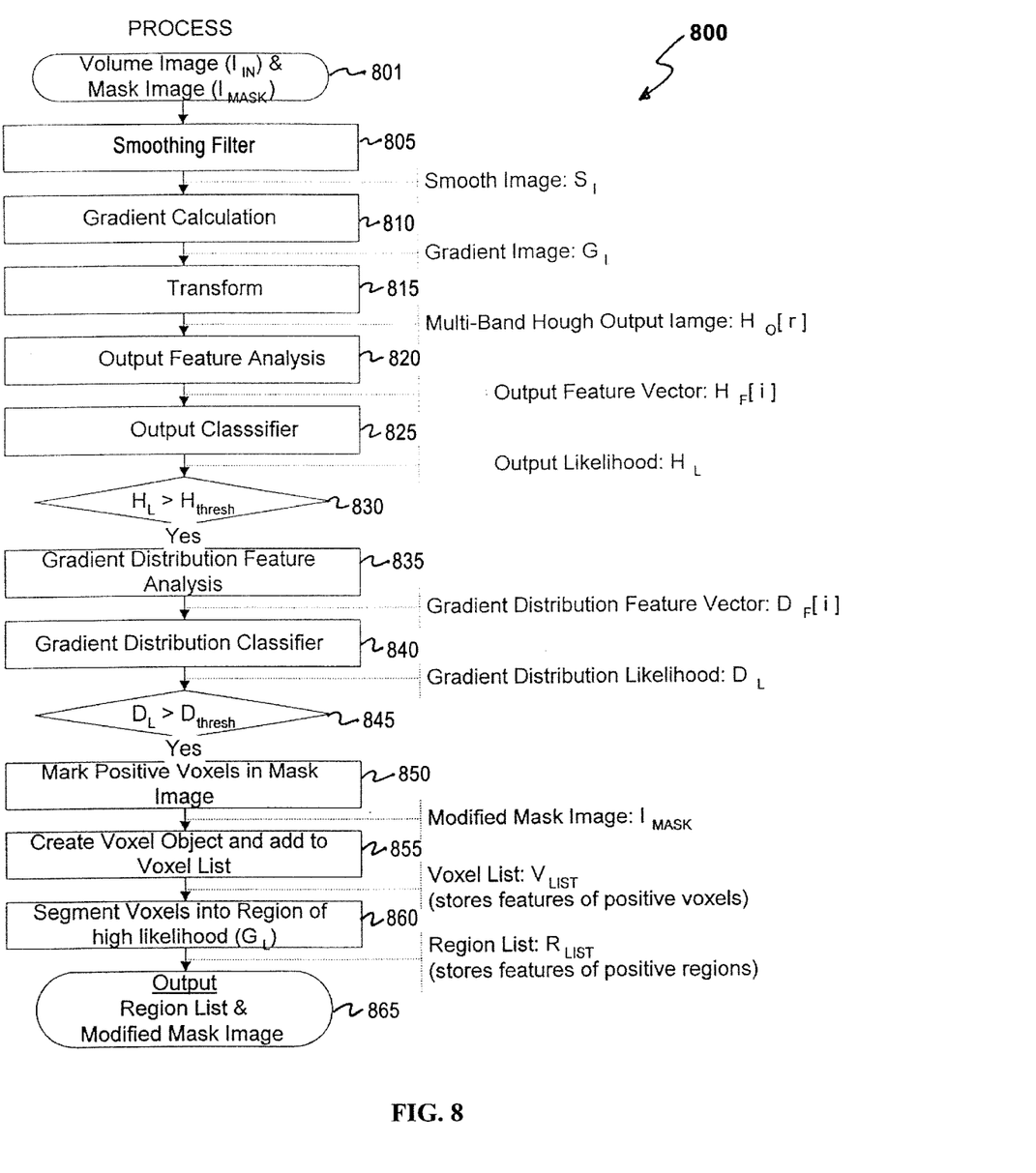
FIG. 8 is a flowchart representing overall steps practiced by a system of the present invention.

One embodiment of the present invention in 3-D is algorithm 800, illustrated in FIG. 8. Input volume data and images, $I_{IN}$, are received at step 801. Three-dimensional digital volume images can be constructed from stacked input slice sections. In one embodiment, digital volumes are created with flexible voxel sizes so that the thickness of the voxels vary. If the voxels are assumed to be isotropic in the X-Y plane then the voxel size in the Z direction is flexible and ranges from nearly isotropic for thin slices to thicker slices comprising many digital slices.

A digital image volume may be subject to noise and interference from several sources including sensor noise, film-grain noise and channel errors. At step 805, optional, but preferable, noise reduction and cleaning is performed on the image volume and image mask created at step 801. Various statistical filtering techniques, including various known linear and non-linear noise-cleaning or processing techniques, can reduce noise effects. Step 805 also includes a smoothing operation that is applied to the whole image volume or partial image volume to reduce the graininess of the image and create a smooth image, $S_f$. Various smoothing techniques are known in the art and are further described in co-pending applications referenced above, such as "Lung Field Segmentation From CT Thoracic Images" application.

One effective 3-D smoothing filter for smoothing the input image is a 3-D Gaussian filter. For such a filter, the size of the Gaussian kernel used in the smoothing operation can be a tuning parameter. In one embodiment, the output ($I_{SMOOTH}$) is stored in a circular buffer in the scan direction and centered on the leading edge of the window of interest (WOI), discussed below (see FIG. 10), within which the gradient calculation is performed.

Potential candidate nodules in volumetric digital images can be considered as local high-density lines around a mass. However, potential candidate nodules sometimes exhibit a very weak contrast and tend to be missed by simple thresholding techniques. Instead, and similar to the analysis described above, a gradient operation is performed on the voxel. At step 810 a 3-D gradient calculation is performed on the smoothed image, $S_f$, to generate a gradient image, $G_f$.

In a preferred approach for step 810, a gradient vector is calculated for each voxel in the input image in the x-, y- and z-directions. The smoothed image ($S_i$) and voxel dimensions ($R_x$, $R_y$, $R_z$) are used for this calculation:

$$G_x(x, y, z) \equiv (S_x(x+1, y, z) - S_x(x-1, y, z))/R_x \quad (1)$$
$$G_y(x, y, z) \equiv (S_x(x, y+1, z) - S_x(x, y-1, z))/R_y$$
$$G_z(x, y, z) \equiv (S_x(x, y, z+1) - S_x(x, y, z-1))/R_z$$

For thick slice data where the voxel size in a dimension, e.g., the z-direction, is large, an interslice gradient can be calculated between slices. This makes the effective gradient image size in the z-direction (2*Depth−1) where Depth is the size of the original image in the z-direction for thick slice volumes. For thick slice volumes, the interslice gradient can be calculated as:

$$G_x\left(x, y, z + \frac{1}{2}\right) \equiv (G_x(x, y, z+1) + G_x(x, y, z))/2 \quad (2)$$
$$G_y\left(x, y, z + \frac{1}{2}\right) \equiv (G_y(x, y, z+1) + G_y(x, y, z))/2$$
$$G_z\left(x, y, z + \frac{1}{2}\right) \equiv (S_x(x, y, z+1) - S_x(x, y, z))/(0.5 \times R_z)$$

At step 815, the gradient vector, $G_f$ (equal to the sum of the vectors $G_x$, $G_y$, and $G_z$), obtained from the gradient calculation at 810 is input to a transform.

Various mathematical operations can be performed to extract information from the gradient calculation 810. For example, the Hough transformation allows a family of lines passing through a common point in the x-y-z domain to map into a connected set of points for a spherical pattern. As applied to spherical 3-D detection at step 815, the Hough transform would be effective in the detection and analysis of spherical-related features (step 820). Hough transformations of the gradients may yield certain parametric curve features that, as applied to a volume can be effective in detecting globular-shaped nodules, 3-D spiculations and other rounded but connected masses. Alternatively, the processes detailed in conjunction with FIGS. 5–7 can be used to identify nodules.

At step 815, the transform operates on the gradients determined above to detect information related to a predetermined pattern. The gradient information from a voxel is effectively dispersed to nearby voxels through a classification procedure detailed below.

At step 820, the dispersed information obtained by a voxel from vector gradients of other voxels can be aggregated through various techniques. For example, the output region for the transform operation at step 815 can be divided into one or more radial zones. In one approach a transform output from a voxel will be assigned to a radial zones associated with the output on the basis, for example, of the magnitude of a value associated with the voxel. The information aggregated at step 820 can be processed to extract information regarding the likelihood of nodule detection at a voxel location (x, y, z).

Figure 9:
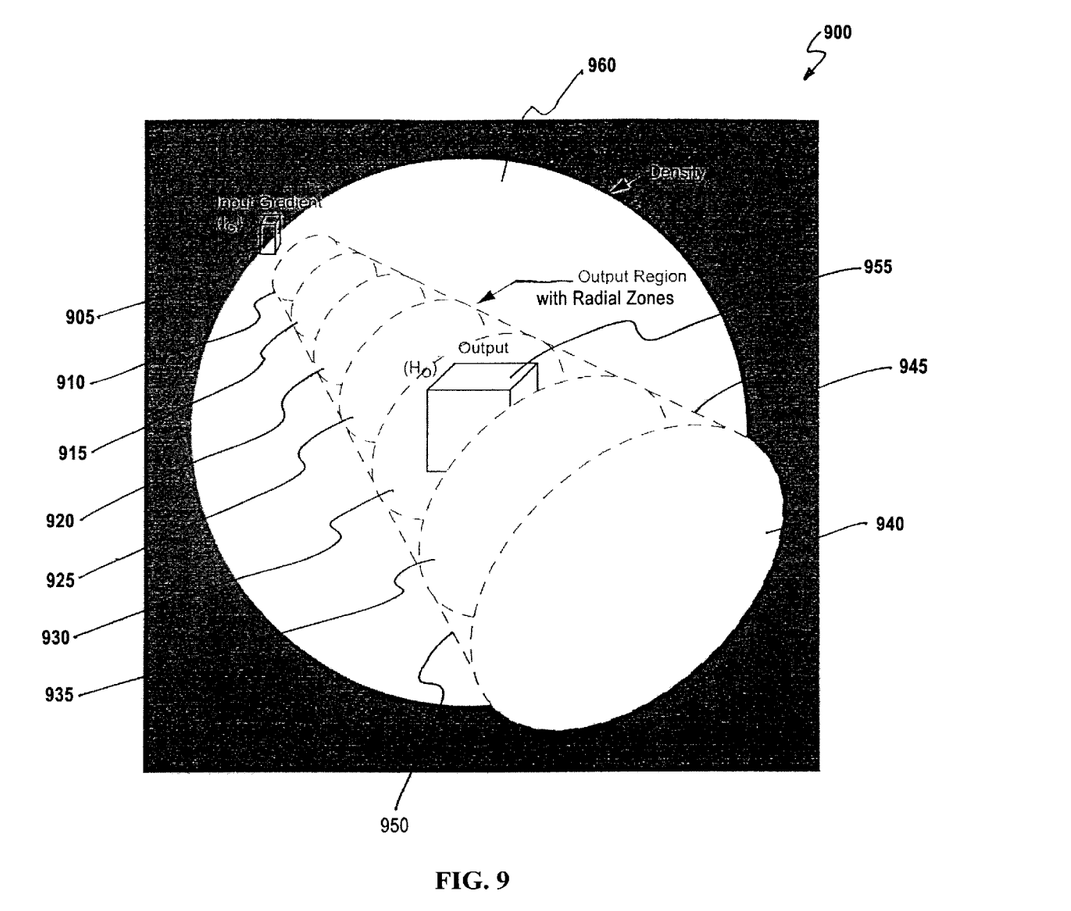
FIG. 9 is a representation of one approach using radial zones for output voxels.

FIG. 9 depicts a sample output feature analysis and output classifiers embodiment corresponding to step 820. A sample nodule 960 is shown having an input gradient 905. The input gradient is associated with a voxel location (x, y, z) located on the edge of the 3-D nodule 960. The gradient is generally a local maximum for those locations where there is likely to be a nodule edge.

In FIG. 9, radial zones are shown with two radial lines 945 and 950 in a direction outward from the gradient location.

The algorithm maintains two accumulations. One accumulation keeps a "probability of not directed" sum of the gradient voxels that point towards the output voxel and the other accumulation keeps the sum of the intensity of those gradient voxels. There are a plurality of radial zones 905 through 940, the smallest zone 905 being closest to the voxel having the input gradient and the furthest zone 940 having the largest radius. The gradient direction determined above dictates the direction of the radial zones emanating from a voxel. Each radial zone, R, encompasses locations in a cumulative array C", each of which has associated with it a value that is incremented whenever that location falls within a radial zone associated with one of the voxels.

The lines are shown diverging away from gradient 905. This divergence is based on the idea that intensity radiates outward from a location; and accordingly the radial zones are shown expanding in a direction away from the gradient 905. Such a divergence, while not a requirement, provides for refinement in accumulating the effect of voxel gradients. An array associated with each voxel includes array dimensions for purposes of tracking and aggregating the total informational content associated with a particular location.

$$H_{O,\ Count}(\tilde{R}) = \text{Sum of } (1 - P(r)) \text{ of directed gradient voxel in Zone (}\tilde{\text{R}}\text{)}$$

$$H_{O,\ Sum}(\tilde{R}) = \text{Sum of Magnitudes of directed gradient voxel in Zone R} \quad (4)$$

where P(r) is based on the output region geometry (such as that of the Hough transform described above) and is a function of the distance (r) from the gradient voxel to the output voxel:

$$P(\vec{r}) \text{ Probability of a random gradient being directed inward:} = \text{Directed Solid Angle}/(4\pi r^2) \quad (5)$$

where $V_{Directed}(\tilde{R})$ Volume of directed output region for Zone R $V_{Total}(\tilde{R})$ Volume of non-directed output region for Zone R From these accumulations, the count and average value of inward (or outward) facing gradient voxels can be calculated for each radial zone.

For normalization purposes, a non-directional transform is also preferably performed. The non-directional transform can be important in the case where some of the gradient voxels surrounding an output voxel are not available (edge of volume) or are excluded (pre-segmentation excludes portions of the volume). In a transform of the present invention, a count is accumulated into all transformed output voxels in a sphere surrounding the gradient voxel. In this transform, there are two similar output accumulations for each radial zone. One output accumulation keeps a "probability of directed" sum of the gradient voxels and the other keeps the variance sum of the gradient voxels.

$H_{O, TotalCount}(\tilde{R})$ Sum of P(r) of gradient voxel in Zone R $H_{O, VarianceSum}(\tilde{R})$ Sum of P(r)*(1−P(r)) of gradient voxel in Zone R From these accumulations, the number of inward directed gradients can be normalized by the expected number of inward (or outward) directed gradient voxels due to a random distribution of gradients and can be calculated for each radial zone.

Once the cumulation into transformed output voxels is complete, features are calculated for each voxel at step 820. In one approach, the expected counts of directed gradient voxels from a random distribution of gradients are initially calculated for each radial zone:

$$H_{F,ExpectedCount}(R) \equiv H_{O,TotalCount}(R) \times \frac{V_{Directed}(R)}{V_{Total}(R)} \quad (6)$$

For each radial zone, the normalized counts ($H_{F, NormalizedCount}(R)$) and the gradients ($H_{F,Gradient}(R)$) are calculated:

$$H_{F,NormalizedCount}(R) \equiv \frac{H_{O,Count}(R) - H_{O,TotalCount}(R)}{\sqrt{H_{O,VarianceCount}(R)}} \quad (7)$$

$$H_{F,Gradient}(R) \equiv \frac{H_{O,Sum}(R)}{H_{O,Count}(R)}$$

The shape of these functions is analyzed to estimate the size, contrast and sharpness of the detected nodule.

Next, the range of radial zones ($R_{min}$ to $R_{max}$) that maximizes the following metric is found $$H_{F, Metric1} = H_{F, NormalizeCount} \times H_{F, AverageGradient} \quad (8)$$

where $H_{F, AverageNormalizedCount}$ measures the number of directed gradients normalized by the number of directed gradients expected from a random distribution of gradients:

$$H_{F,AverageNormalizedCount} \equiv \frac{\sum_{R=R_{min}}^{R_{max}} H_{O,Count}(R) - \sum_{R=R_{min}}^{R_{max}} H_{F,ExpectedCount}(R)}{\sum_{R=R_{min}}^{R_{max}} H_{F,ExpectedCount}(R)} \quad (9)$$

and $H_{F,AverageNormalizedCount}$ is the average gradient:

$$H_{F,AverageGradient} \equiv \frac{\sum_{R=R_{min}}^{R_{max}} H_{O,Sum}(R)}{\sum_{R=R_{min}}^{R_{max}} H_{F,Count}(R)} \quad (10)$$

All of the above-described features can be input to a classifier that estimates the likelihood that a particular voxel is associated with the center of a nodule.

At step 825, the above-described features are input to a neural network classifier that estimates the likelihood that the voxel is at the center of a nodule ($H_L$). Step 830 indicates that only voxels that are above the threshold $H_{thresh}$ are processed further.

Statistics about the distribution of outward facing gradients that surround a given voxel are calculated and processed at step 835. From such statistics, features are calculated that characterize the size and shape of the distribution of gradients. A well-defined nodule will have an even distribution. The features can be used to differentiate various shapes, such as spherical shapes (nodule) or cylindrical shapes (vessel). In the case of a cylinder, size and direction estimations are calculated. In the case of a sphere, size and shape estimations are calculated. Geometric moment statistics can used to calculate distribution shape features. Such features include size, eccentricity and irregularity.

In one approach, the vertices of a poly-tetrahedron are used to divide spherical direction into 'N' evenly spaced sectors. The distribution of gradients in the sectors that surround the output voxel are used to calculate features that characterize the completeness and shape of the distribution.

At step 840, the above-described features are input to a neural network classifier that estimates the likelihood that the voxel is at the center of a nodule ($D_L$). At step 845, only voxels that are above the threshold $D_{thresh}$ will be processed further.

At step 850, voxels that pass the threshold $D_{thresh}$ are marked in the mask image with a scale value that is proportional the gradient distribution likelihood $D_L$.

For each voxel that exceed the threshold $D_{thresh}$ intensity, a voxel object structure, or array, is created to hold features and likelihood values. These objects are added to a voxel object list at step 855.

Thereafter, at step 860 regions of voxels with high likelihood are segmented, using known segmentation techniques, and collected into a list of ROIs. Features and likelihood from the segmented voxels are summarized and stored in ROI objects.

To minimize memory usage and system requirements, various operations of the algorithm are preferably performed in one pass through the volume using buffers to hold intermediate results. Instead of performing computations in the entire 3-D image volume to be processed, a window of interest (WOI) is employed using voxels sandwiched between planes (see FIG. 10). A WOI starts at one end of the volume 1010 and move through the volume, for example, in a z-direction. Intermediate results are determined with respect to the WOI between planes 1020 and 1040. Advantageously, a given voxel in the digital volume image is effectively considered with respect to only a part of the entire volume being processed (i.e., in the WOI) and results in a reduced computational burden. Thus, the method used in a process according to the present invention can be very fast and efficient. Moreover, the method is highly amenable to hardware implementation using parallel processors, thus increasing the speed of a CAD digital acquisition system even further.

To assure adequate detection of nodules in a volume 1010, the size of the WOI can be varied to be any size. For example, the WOI in FIG. 10 between planes 1020 and 1040 can be adjusted to have any thickness in the z-direction.

Figure 10:
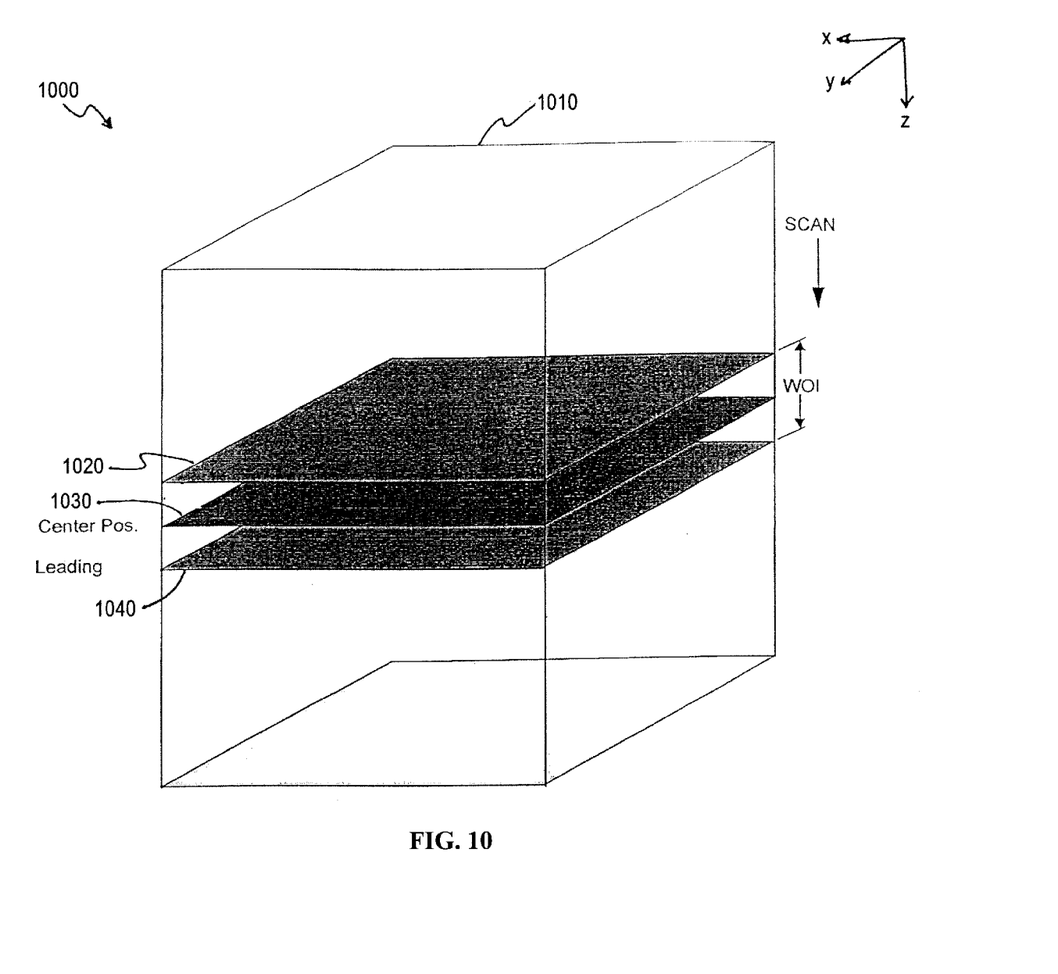
FIG. 10 is a representation of a single pass calculation in a digital volume in accordance with the present invention.

In one approach, the thickness of the WOI is selected to be twice the maximum nodule radius ($R_{MAX}$). Optionally, a buffer memory can be used wherein only the results in the WOI are stored. If no abnormality is detected within a WOI, then the buffer can be reset over and over until a possible abnormality is identified. Potential nodule locations and nodule information can be stored, and the buffer initialized for the detection of additional abnormalities.

There are two positions in the WOI where calculations are performed. The first position is the leading edge 1040 of the WOI where the Gaussian filter, gradient calculation and the transform are performed. The second position is at the center 1030 of the WOI where the accumulation is complete and surrounding gradient data is available.

Like the pixel-based detection algorithm, the voxel-based detection algorithm is a "forward direction" algorithm. Each voxel in a WOI is processed only once in generating the cumulative array value. Furthermore, a lookup table procedure can be used which ultimately maps the output of a transform operation into radial zones of covered voxels in the cumulative array C", based on the shape of the predetermined pattern.

As with the 2-D case, the lookup table procedure for mapping points and directions into regions of potential intersection can incorporate weighting values in the predetermined pattern. Thus, instead of simply adding a "1" to the cumulative array C" for every array location falling inside the pattern, a weighting value may be used. In one approach, the weighting value can be used to select an appropriate radial zone associated with a intensity gradient for a voxel.

In this application, an efficient method for 3-D nodule detection from 3-D digital images is presented. The present invention provides a system and method that is accurate, efficient, flexible and detects pleural nodules that prior systems and approaches overlook or are incapable of detecting. The foregoing examples illustrate certain exemplary embodiments of the invention from which other obvious embodiments, variations, and modifications will be apparent to those skilled in the art. The invention should therefore not be limited to the particular embodiments discussed above, but rather is defined by the claims.

What is claimed is:

1. A method of determining regions of interest in an image that is an array of image elements comprising the steps of:
    at each image element in the image, determining if the image element contains an edge and determining a gradient of the edge, if any;
    generating a cumulative array of cells that identifies regions of interest in the image by:
        at each image element in the image that contains an edge, using the gradient to define a region in the cumulative array in a direction specified by said gradient, and
        at each cell in the cumulative array within the region defined with the gradient, incrementing a numerical value associated with the cell; and
    identifying regions of interest in the image by identifying those cells in the cumulative array that have numerical values that are local extrema.

2. The method of claim 1 further comprising the step of thresholding the cumulative array to identify regions of interest near locations where said cumulative array exceeds a threshold value.

3. The method of claim 1 wherein the step of determining the gradient comprises determining a gradient intensity value and a gradient direction value; and the step of using the gradient to define a region of interest uses the gradient intensity value and gradient direction value of the image elements.

4. The method of claim 3 wherein, for each region defined in the cumulative array, each cell in the cumulative array within that region is incremented by a numerical value corresponding to the gradient intensity value for the image element associated with that region.

5. The method of claim 1 wherein the region in the cumulative array is spaced from a projection of the image element onto the cumulative array and is aligned with the gradient direction value.

6. The method of claim 5 wherein the region extends from a first radial distance to a second radial distance from the projection of the image element onto the cumulative array.

7. The method of claim 1 wherein the region in the cumulative array is a volume extending from a first radial distance to a second radial distance from the projection of the image element onto the cumulative array and bounded by lines radiating from said projection.

8. The method of claim 1 wherein each image element is a voxel.

9. The method of claim 1 wherein the edge is detected by a Sobel operator.

10. The method of claim 1 wherein the region of interest is a lung nodule.

11. A method of detecting regions of interest in an image composed of volume elements (voxels) comprising the steps of:
    calculating gradient vectors for voxels having edges, each said vector having a magnitude and a direction;
    applying a transform to the gradient vectors to create a transform output;
    classifying the transform output into output regions by projecting the transform output onto a cumulative array using the vector magnitudes and directions;
    accumulating the transform output as numerical values in the cumulative array; and
    processing the cumulative array to detect regions of interest by identifying numerical values that are local extrema.

12. The method of claim 11 wherein the step of calculating gradient vectors is performed for a voxel in a window of interest of the image.

13. The method of claim 11 further including the step of initializing the cumulative array.

14. The method of claim 11 wherein the output regions represent a range of probabilities concerning the vector directions.

15. The method of claim 11 wherein substantially every voxel is examined to determine if it contains an edge.

16. The method of claim 11 wherein the step of accumulating the transform output comprises the step of accumulating in the cumulative array the transform output for each gradient vector.

17. The method of claim 11 wherein the cumulative array is incremented at array locations defined by a predetermined pattern extending from a voxel in the direction of the gradient vector calculated for that voxel.

18. The method of claim 17 wherein the predetermined pattern subtends an angle at the projection of the voxel onto the cumulative array and extends between a first radial distance and a second radial distance from said projection.

19. The method of claim 18 wherein the first radial distance and the second radial distance are selected according to the size of a desired region of interest.

20. The method of claim 11 wherein the step of accumulating the transform output comprises the step of incrementing by a first amount cells in the cumulative array within a volume oriented by the gradient vector.

21. A method of determining regions of interest in an image that is an array of image elements comprising the steps of:
    at each image element in the image, determining if the image element contains a line and determining a direction of the line, if any;
    generating a cumulative array of cells that identifies regions of interest in the image by:
        at each image element in the image that contains a line, using the direction of the line to define a region in the cumulative array having an orientation specified by said direction, and
        at each cell in the cumulative array within the defined region, incrementing a numerical value associated with the cell; and
    identifying regions of interest in the image by identifying those cells in the cumulative array that have numerical values that are local extrema.

22. The method of claim 21 further comprising the step of thresholding the cumulative array to identify regions of interest near locations where said cumulative array exceeds a threshold value.

23. The method of claim 21 wherein the region in the cumulative array is spaced from a projection of the image element onto the cumulative array and is aligned with the direction of the line.

24. The method of claim 23 wherein the region extends from a first radial distance to a second radial distance from the projection of the image element onto the cumulative array.

25. The method of claim 21 wherein the region in the cumulative array is a volume extending from a first radial distance to a second radial distance from the projection of the image element onto the cumulative array and bounded by lines radiating from said projection.

26. The method of claim 21 wherein each image element is a voxel.

27. The method of claim 21 wherein the region of interest is a spiculated mass.

* * * * *